United States Patent
Jacofsky et al.

(10) Patent No.: US 9,861,829 B2
(45) Date of Patent: *Jan. 9, 2018

(54) COLD PLASMA ELECTROPORATION OF MEDICATION AND ASSOCIATED METHODS

(71) Applicant: Plasmology4, Inc., Scottsdale, AZ (US)

(72) Inventors: Marc C. Jacofsky, Phoenix, AZ (US);
David J. Jacofsky, Peoria, AZ (US);
Gregory A. Watson, Lake Mary, FL (US)

(73) Assignee: Plasmology4, Inc., Scottsdale, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/376,289

(22) Filed: Dec. 12, 2016

(65) Prior Publication Data
US 2017/0087372 A1   Mar. 30, 2017

Related U.S. Application Data

(63) Continuation of application No. 14/145,320, filed on Dec. 31, 2013, now Pat. No. 9,521,736.
(Continued)

(51) Int. Cl.
*A61M 35/00* (2006.01)
*A61N 1/44* (2006.01)
(Continued)

(52) U.S. Cl.
CPC ........... *A61N 1/44* (2013.01); *A61B 17/3421* (2013.01); *A61N 1/327* (2013.01); *A61B 2017/3454* (2013.01); *H05H 1/2406* (2013.01)

(58) Field of Classification Search
CPC ........ A61L 2/14; A61L 2/0094; A61M 15/02; A61M 16/12; A61N 1/40; A61N 1/44;
(Continued)

(56) References Cited

U.S. PATENT DOCUMENTS 2,927,322 A   3/1960   Simon et al.
3,432,722 A   3/1969   Naydan et al.
(Continued)

FOREIGN PATENT DOCUMENTS

WO   WO 2005/084569 A1   9/2005
WO   WO 2006/116252      11/2006
(Continued)

OTHER PUBLICATIONS

International Search Report dated Mar. 21, 2014 for Appl. No. PCT/US2013/078523, 3 pages.
(Continued)

*Primary Examiner* — Gerald Landry, II
(74) *Attorney, Agent, or Firm* — Sterne, Kessler, Goldstein & Fox P.L.L.C.

(57) ABSTRACT

A method and device to apply a cold plasma to a substance at a treatment surface of a patient to cause electroporation of the substance into cells of the patient. The substance can be previously applied to the treatment surface. Alternatively, the substance can be placed in a foam-like material within a tip that passes the cold plasma from the cold plasma device to the treatment area. The tip can be a cannula device with an aperture at the distal end. The cannula device can also have apertures along a portion of the length of the cannula device.

20 Claims, 6 Drawing Sheets

Related U.S. Application Data

(60) Provisional application No. 61/747,871, filed on Dec. 31, 2012.

(51) Int. Cl.
  *A61N 1/32* (2006.01)
  *A61B 17/34* (2006.01)
  *H05H 1/24* (2006.01)

(58) Field of Classification Search
  CPC ...... A61N 1/327; H05H 1/46; H05H 2240/20; H05H 2245/122; H05H 2277/10
  USPC ....... 315/111.21, 111.91; 604/23; 606/32, 41
  See application file for complete search history.

(56) References Cited

U.S. PATENT DOCUMENTS

| | | | |
|---|---|---|---|
| 3,487,414 A | 12/1969 | Booker | |
| 3,735,591 A | 5/1973 | Burkhart | |
| 4,088,926 A | 5/1978 | Fletcher et al. | |
| 4,365,622 A | 12/1982 | Harrison | |
| 4,380,320 A | 4/1983 | Hollstein et al. | |
| 4,422,013 A | 12/1983 | Turchi et al. | |
| 4,781,175 A | 11/1988 | McGreevy et al. | |
| 5,079,482 A | 1/1992 | Villecco et al. | |
| 5,216,330 A | 6/1993 | Ahonen | |
| 5,225,740 A | 7/1993 | Ohkawa | |
| 5,282,861 A * | 2/1994 | Kaplan | A61F 2/28 427/2.26 |
| 5,304,888 A | 4/1994 | Gesley et al. | |
| 5,698,164 A | 12/1997 | Kishioka et al. | |
| 5,876,663 A | 3/1999 | Laroussi | |
| 5,883,470 A | 3/1999 | Hatakeyama et al. | |
| 5,909,086 A | 6/1999 | Kim et al. | |
| 5,961,772 A | 10/1999 | Selwyn | |
| 5,977,715 A | 11/1999 | Li et al. | |
| 6,032,077 A * | 2/2000 | Pomeranz | A61B 17/00234 606/32 |
| 6,096,564 A | 8/2000 | Denes et al. | |
| 6,099,523 A | 8/2000 | Kim et al. | |
| 6,113,851 A | 9/2000 | Soloshenko et al. | |
| 6,204,605 B1 | 3/2001 | Laroussi et al. | |
| 6,225,593 B1 | 5/2001 | Howieson et al. | |
| 6,228,330 B1 | 5/2001 | Herrmann et al. | |
| 6,262,523 B1 | 7/2001 | Selwyn et al. | |
| 6,441,554 B1 | 8/2002 | Nam et al. | |
| 6,455,014 B1 | 9/2002 | Hammerstrom et al. | |
| 6,520,950 B1 | 2/2003 | Hofmann et al. | |
| 6,611,106 B2 | 8/2003 | Monkhorst et al. | |
| 6,667,007 B1 | 12/2003 | Schmidt | |
| 6,956,329 B2 | 10/2005 | Brooks et al. | |
| 6,958,063 B1 | 10/2005 | Soll et al. | |
| 7,006,874 B2 | 2/2006 | Knowlton et al. | |
| 7,011,790 B2 | 3/2006 | Ruan et al. | |
| 7,037,468 B2 | 5/2006 | Hammerstrom et al. | |
| 7,081,711 B2 | 7/2006 | Glidden et al. | |
| 7,094,314 B2 | 8/2006 | Kurunczi | |
| 7,192,553 B2 | 3/2007 | Crowe et al. | |
| 7,215,697 B2 | 5/2007 | Hill | |
| 7,271,363 B2 | 9/2007 | Lee et al. | |
| 7,300,436 B2 | 11/2007 | Penny et al. | |
| 7,445,619 B2 * | 11/2008 | Auge, II | A61B 17/88 606/41 |
| 7,608,839 B2 | 10/2009 | Coulombe et al. | |
| 7,633,231 B2 | 12/2009 | Watson | |
| 7,683,342 B2 | 3/2010 | Morfill et al. | |
| 7,691,101 B2 | 4/2010 | Davison et al. | |
| 7,719,200 B2 | 5/2010 | Laroussi | |
| 7,771,422 B2 * | 8/2010 | Auge, II | A61B 18/14 606/41 |
| 7,777,151 B2 | 8/2010 | Kuo | |
| 7,785,322 B2 | 8/2010 | Penny et al. | |
| 7,799,290 B2 | 9/2010 | Hammerstrom et al. | |
| 8,267,884 B1 | 9/2012 | Hicks | |
| 8,294,369 B1 | 10/2012 | Laroussi | |
| 8,460,283 B1 | 6/2013 | Laroussi et al. | |
| 9,521,736 B2 | 12/2016 | Jacofsky et al. | |
| 2002/0129902 A1 | 9/2002 | Babayan et al. | |
| 2003/0222586 A1 | 12/2003 | Brooks et al. | |
| 2005/0088101 A1 | 4/2005 | Glidden et al. | |
| 2005/0179395 A1 | 8/2005 | Pai | |
| 2006/0009756 A1 * | 1/2006 | Francischelli | A61M 5/14 606/32 |
| 2006/0189976 A1 | 8/2006 | Karni et al. | |
| 2007/0161924 A1 | 7/2007 | Dolphin et al. | |
| 2008/0159925 A1 | 7/2008 | Shimizu et al. | |
| 2009/0188626 A1 | 7/2009 | Lu et al. | |
| 2009/0234269 A1 * | 9/2009 | Tavger | A61M 11/02 604/20 |
| 2009/0248012 A1 * | 10/2009 | Maor | A61B 18/1492 606/41 |
| 2010/0018524 A1 | 1/2010 | Jinks et al. | |
| 2010/0133979 A1 | 6/2010 | Lu | |
| 2010/0139663 A1 | 6/2010 | O'Neil | |
| 2010/0145253 A1 | 6/2010 | Gutsol et al. | |
| 2010/0275950 A1 | 11/2010 | Mack et al. | |
| 2010/0331758 A1 * | 12/2010 | Davalos | A61N 1/327 604/20 |
| 2011/0022043 A1 | 1/2011 | Wandke et al. | |
| 2011/0112528 A1 * | 5/2011 | Stieber | A61L 2/0011 606/41 |
| 2011/0190372 A1 | 8/2011 | Tomic-Canic et al. | |
| 2012/0100524 A1 | 4/2012 | Fridman et al. | |
| 2012/0187841 A1 | 7/2012 | Kindel et al. | |
| 2012/0259270 A1 | 10/2012 | Wandke et al. | |
| 2012/0288934 A1 * | 11/2012 | Weltmann | A61B 18/042 435/375 |
| 2013/0022514 A1 | 1/2013 | Morfill et al. | |
| 2013/0053762 A1 | 2/2013 | Rontal et al. | |
| 2013/0068226 A1 | 3/2013 | Watson et al. | |
| 2013/0068732 A1 * | 3/2013 | Watson | A61M 16/12 219/121.5 |
| 2013/0072861 A1 * | 3/2013 | Watson | A61M 16/12 604/23 |
| 2013/0134878 A1 | 5/2013 | Selwyn | |
| 2013/0199540 A1 | 8/2013 | Buske | |
| 2013/0204068 A1 | 8/2013 | Gnanashanmugam et al. | |
| 2013/0253415 A1 * | 9/2013 | Sano | A61B 18/14 604/20 |
| 2014/0000810 A1 | 1/2014 | Franklin et al. | |
| 2014/0364797 A1 * | 12/2014 | Schoenbach | A61N 1/403 604/20 |

FOREIGN PATENT DOCUMENTS

| | | |
|---|---|---|
| WO | WO 2007/124910 A2 | 11/2007 |
| WO | WO 2010/107722 A1 | 9/2010 |
| WO | WO 2011/055368 A2 | 5/2011 |
| WO | WO 2011/055369 A2 | 5/2011 |
| WO | WO 2011/076193 A1 | 6/2011 |
| WO | WO 2012/106735 A2 | 8/2012 |
| WO | WO 2012/153332 A2 | 11/2012 |
| WO | WO 2013/101673 A1 | 7/2013 |

OTHER PUBLICATIONS

Written Opinion of the International Searching Authority dated Mar. 21, 2014 for Appl. No. PCT/US2013/078523, 6 pages.

Misra et al., "Nonthermal Plasma Inactivation of Food-Borne Pathogens," *School of Food Science and Environmental Health at Dublin Institute of Technology*, 32 pages (2011).

Dumé, Belle, "Cold Plasmas Destroy Bacteria," article, [online], [retrieved on Jan. 5, 2007], Retrieved from the PhysicsWeb website using Internet <URL:http://physicsweb.org/articles/news7/4/19>.

Gould, Phillip and Eyler, Edward, "Ultracold Plasmas Come of Age," article [online], [retrieved on Jan. 5, 2007], Retrieved from the PhysicsWeb website using Internet <URL:http://physicsweb.org/articles/world/14/3/3>.

Schultz, James, "Cold Plasma Ignites Hot Applications," article, [online], [retrieved on Jan. 5, 2007], Retrieved from the Old

(56) References Cited

OTHER PUBLICATIONS

Dominion University website using Internet <URL:http://www.odu.edu/ao/instadv/quest/coldplasma.html>.
Lamba, Bikram, "Advent of Cold Plasma," article, [online], [retrieved on Jan. 5, 2007], Retrieved from the PhysOrg.com website using Internet <URL:http/www.physorg.com/printnews.php?newsid=6688>.
Book of Abstracts, 3rd International Conference on Plasma Medicine (ICPM-3), Sep. 19-24, 2010, International Society for Plasma Medicine.
International Search Report dated Aug. 6, 2008 for Appl. No. PCT/US2008/061240, 1 page.
Written Opinion of International Searching Authority dated Aug. 6, 2008 for Appl. No. PCT/US2008/061240, 6 pages.
Extended European Search Report dated Feb. 8, 2012 for European Patent Appl. No. EP08746627.2, 7 pages.
Pointu et al., "Nitrogen Atmospheric Pressure Post Discharges for Surface Biological Decontamination inside Small Diameter Tubes," *Plasma Process. Polym.* 5:559-568, Wiley-VCH Verlag GmbH & Co. KGaA, Weinheim (2008).
Chakravarthy et al., "Cold Spark Discharge Plasma Treatment of Inflammatory Bowel Disease in an Animal Model of Ulcerative Colitis," *Plasma Medicine* (1)1:3-19, Begell House, Inc. (2011).
Fridman et al., "Comparison of Direct and Indirect Effects of Non-Thermal Atmospheric-Pressure Plasma on Bacteria," *Plasma Processl Polym.*, 4, 370-375, 6 pages, Wiley-VCH Verlag GmbH & Co. KGaA, Weinheim (2007).
Alexander Fridman "Plasma Chemistry," pp. 263-271, Cambridge University Press, 2008, 9 pages.
O'Connell, et al., "The role of the relative voltage and phase for frequency coupling in a dual-frequency capacitively coupled plasma," *Applied Physics Letters*, 93 081502, 3 pages, American Institute of Physics (Aug. 25, 2008).
Nie et al., "A two-dimensional cold atmospheric plasma jet array for uniform treatment of large-area surfaces for plasma medicine," *New Journal of Physics*, 11 115015, 14 pages, IOP Publishing Ltd and Deutsche Physikalische Gesellschaft (2009).
Pompl et al., "The effect of low-temperature plasma on bacteria as observed by repeated AFM imaging," *New Journal of Physics*, 11 115023, 11 pages, IOP Publishing Ltd and Deutsche Physikalische Gesellschaft (Nov. 26, 2009).
Walsh et al., "Three distinct modes in a cold atmospheric pressure plasma jet;" *J. Phys. D.: Appl. Phys.* 43 075201, 14 pages, IOP Publishing Ltd (Feb. 3, 2010).
Ricci et al., "The effect of stochastic electrical noise on hard-to-heal wounds," *Journal of Wound Care*, 8 pages, 19:3 Mark Allen Publishing Ltd ( Mar. 2010).
U.S. Appl. No. 61/485,747, filed May 13, 2011, inventor Thomas J, Sheperak, 14 pages.
Liu et al., "Sub-60° C. atmospheric helium-water plasma jets: modes, electron heating and downstream reaction chemistry," *J. Phys. D: Appl. Phys.* 44 345203, 13 pages, IOP Publishing Ltd. (Aug. 11, 2011).
Pei et al., "Inactivation of a 25.5 μm *Enterococcus faecalis* biofilm by a room-temperature, battery-operated, handheld air plasma jet," *J. Phys. D. Appl. Phys.*, 45 165205, 5 pages, IOP Publishing Ltd (Apr. 4, 2012).

Walsh et al., "Chaos in atmospheric-pressure plasma jets," *Plasma Sources Sci. Technol.*, 21 034008, 8 pages, IOP Publishing Ltd (May 2, 2012).
Banu, et al., "Cold Plasma as a Novel Food Processing Technology," *International Journal of Emerging trends in Engineering and Development*, Issue 2, vol. 4, ISSN 2249-6149, pp. 803-818, 16 pages (May 2012).
Dobrynin, et al., "Live Pig Skin Tissue and Wound Toxicity of Cold Plasma Treatment," *Plasma Medicine*, 1(1):93-108, 16 pages, Begell House, Inc. (2011).
Fernández, et al., "The inactivation of *Salmonella* by cold atmosphere plasma treatment," *Food Research International*, 45:2, 678-684, 7 pages, Elsevier Ltd. (Mar. 2012).
Tien, et al., "The Bilayer Lipid Membrane (BLM) Under Electrical Fields," *IEEE Transactions on Dielectrics and Electrical Institute*, 10:5, 717-727, 11 pages (Oct. 2003).
Jayaram et al.., "Optimization of Electroporation Waveforms for Cell Sterilization," *IEEE Transactions on Industry Applications*, 40:6, 1489-1497, 9 pages (2004).
Fridman, et al., "Use of Non-Thermal Atmospheric Pressure Plasma Discharge for Coagulation and Sterilization of Surface Wounds," *IEEE International Conference on Plasma Science*, Abstract, p. 257, 1 page (Jun. 2005).
Fridman, et al., "Use of Non-Thermal Atmospheric Pressure Plasma Discharge for Coagulation and Sterilization of Surface Wounds," 6 pages (Jun. 2005).
Fridman, et al., "Blood Coagulation and Living Tissue Sterilization by Floating-Electrode Dielectric Barrier Discharge in Air," *Plasma Chem Plasma Process*, 26: 425-442, 18 pages, Springer Science Business Media, Inc. (2006).
Gurol, et al., "Low Temperature Plasma for decontamination of *E. coli* in milk," *International Journal of Food Microbiology*, 157: 1-5, 5 pages, Elsevier B.V. (Jun. 2012).
Lado, et al., "Alternative food-preservation technologies: efficacy and mechanisms," *Microbes and Infection*, 4: 433-440 8 pages, Elsevier SAS (2002).
Leduc, et al., "Cell permeabilization using a non-thermal plasma," *New Journal of Physics*, 11: 115021, 12 pages, IOP Publishing Ltd and Deutsche Physikalisehe Gesellschaft (2009).
Machado, et al., "Moderate electric fields can inactivate *Escherichia coli* at room temperature," *Journal of Food Engineering*, 96: 520-527, 8 pages, Elsevier Ltd. (2009).
Li, et al., "Optimizing the distance for bacterial treatment using surface micro-discharge plasma," *New Journal of Physics*, 14: 023058, 11 pages, IOP Publishing Ltd and Deutsche Physikalische Gesellschaft (Feb. 2012).
Morfill, et al., "Nosocomial infections—a new approach towards preventive medicine using plasmas," *New Journal of Physics*, 11: 115019, 10 pages, IOP Publishing Ltd and Deutsche Physikalische Gesellschaft (2009).
Nian, et al., "Decontamination of *Salmonella* on Sliced Fruits and Vegetables Surfaces using a Direct-Current, Atmospheric-Pressure Cold Plasma," *IEEE International Conference on Plasma Science*, p. 1, 1 page (Jun. 2011).
Toepfl, ei al., "High intensity pulsed electric fields applied for food preservation," *Chemical Engineering and Processing*, 46: 537-546, 10 pages, Elsevier B.V. (2007).

* cited by examiner

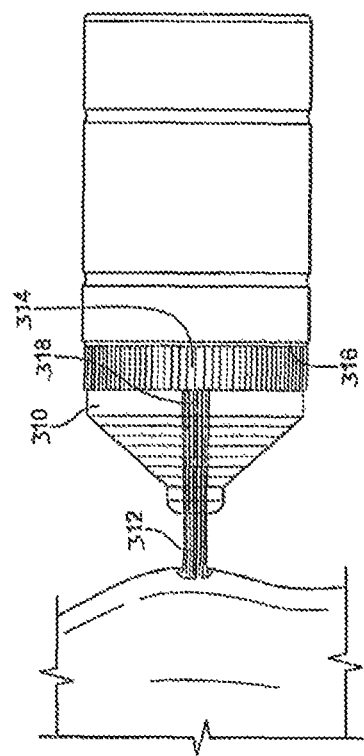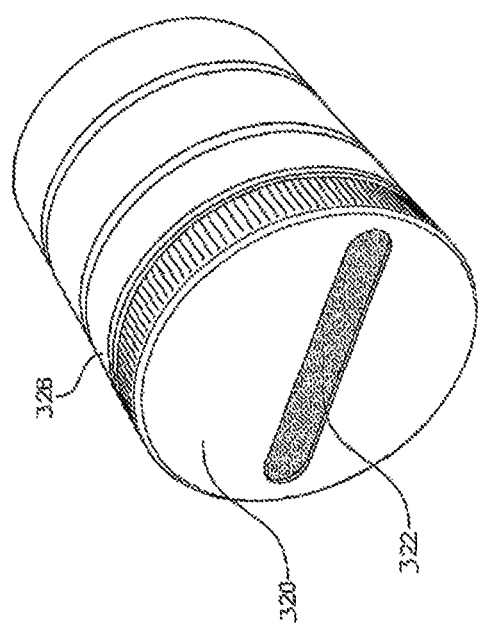

COLD PLASMA ELECTROPORATION OF MEDICATION AND ASSOCIATED METHODS

CROSS-REFERENCE TO RELATED APPLICATIONS

This application is a continuation of U.S. application Ser. No. 14/145,320, filed Dec. 31, 2013, which claims the benefit of U.S. Provisional Application No. 61/747,871, filed Dec. 31, 2012 and entitled "Cold Plasma Electroporation of Medication and Associated Methods," all of which are incorporated herein by reference in their entirety.

This application is related to U.S. Provisional Application No. 60/913,369, filed Apr. 23, 2007; U.S. patent application Ser. No. 12/038,159, filed Feb. 27, 2008 (which issued as U.S. Pat. No. 7,633,231); U.S. patent application Ser. No. 13/620,118, filed Sep. 14, 2012; and U.S. patent application Ser. No. 13/620,236, filed Sep. 14, 2012, each of which are herein incorporated by reference in their entireties.

BACKGROUND

Field of the Art

The present invention relates to devices and methods for cold plasma medical treatment, and, more particularly, to such devices and methods for cold plasma electroporation of medications and bioactive agents into cells.

Background Art

Cold plasmas (i.e., non-thermal plasmas) are produced by the delivery of pulsed high voltage signals to a suitable electrode. Cold plasma devices may take the form of a gas jet device or a dielectric barrier discharge (DBD) device.

Electroporation is the process of exposing cells to electrical fields, as illustrated in FIG. 1. When a biological cell 180 is exposed to programmed electric pulses from electrodes 170, the lipid membrane of the cell can be altered and become permeable 160. The change in the cell membrane may be of a plastic (temporary) or permanent nature, and these changes are commonly referred to as reversible or irreversible permeabilization, respectively.

One of the primary reasons to electroporate a cell, or group of cells, is to transport a molecule across the membrane that otherwise would be unable to cross this barrier, or would require cellular energy to pump/transport in the absence of applied energy. Therefore electroporation allows the cell membrane to become permeablized, and is frequently used to either insert proteins 110 into the cell membrane, introduce large 130 or small 120 molecules into the cell(s), induce cellular fusion 140, or to destroy the cell membrane 150 altogether.

Irreversible premeabilization can permanently damage a cell and lead to apoptosis or other mechanisms of cell death. Controllable apoptosis has been used in biofouling control, debacterialization, and drug-free cancer therapies.

Reversible electroporation is primarily used as a method of molecular delivery, transferring a wide array of molecules, such as drugs, ions, dyes, tracers, oligonucleotides, RNA, antibodies, proteins, etc., into and out of cells. There are several advantages to using electroporation-moderated molecular delivery over conventional methods. Electroporation is generally non-invasive, drug free, non-toxic and rapidly accomplished. Due to the fact that electroporation is a physical process between the supplied electric field and the cell membrane, it is less influenced by the specific cell type when compared to conventional methods.

Electroporation is demonstrably effective in both in vivo and in vitro clinical studies and applications, and has been employed for treating various cancers including lung, skin, breast, leukemia, specific bone cancers, and for DNA vaccination.

BRIEF SUMMARY OF THE INVENTION

An embodiment is described of a method of applying a substance to a treatment area of a patient. The method also includes applying a cold plasma from a cold plasma device to the substance for a predetermined treatment time to thereby cause electroporation of the substance into cells of the patient.

A further embodiment is described of a method of generating a cold plasma from a cold plasma device. The method also includes passing the cold plasma from the cold plasma device via a nozzle to a treatment area of a patient for a predetermined treatment time. The nozzle includes an element (e.g., disk) positioned in the nozzle, the element (e.g., disk) including a substance. The passing of the cold plasma through the substance thereby causes electroporation of the substance into cells of the patient.

BRIEF DESCRIPTION OF THE DRAWINGS/FIGURES

FIGS. 3A and 3B illustrate different tips for use with a cold plasma generation device, in accordance with an embodiment of the present invention.

DETAILED DESCRIPTION OF THE INVENTION

Cold temperature plasmas have attracted a great deal of enthusiasm and interest by virtue of their provision of plasmas at relatively low gas temperatures. The provision of plasmas at such a temperature is of interest to a variety of applications, including wound healing, anti-bacterial processes, various other medical therapies and sterilization. As noted earlier, cold plasmas (i.e., non-thermal plasmas) are produced by the delivery of pulsed high voltage signals to a suitable electrode. Cold plasma devices may take the form of a gas jet device or a dielectric barrier discharge (DBD) device. In the context of this application, the methods disclosed herein can be used with any platform for the generation of cold plasma. Accordingly, the methods are not limited to the use of a DBD device, a gas jet device, or a cold plasma generated using a multi-frequency harmonic-rich power supply.

Figure 1:
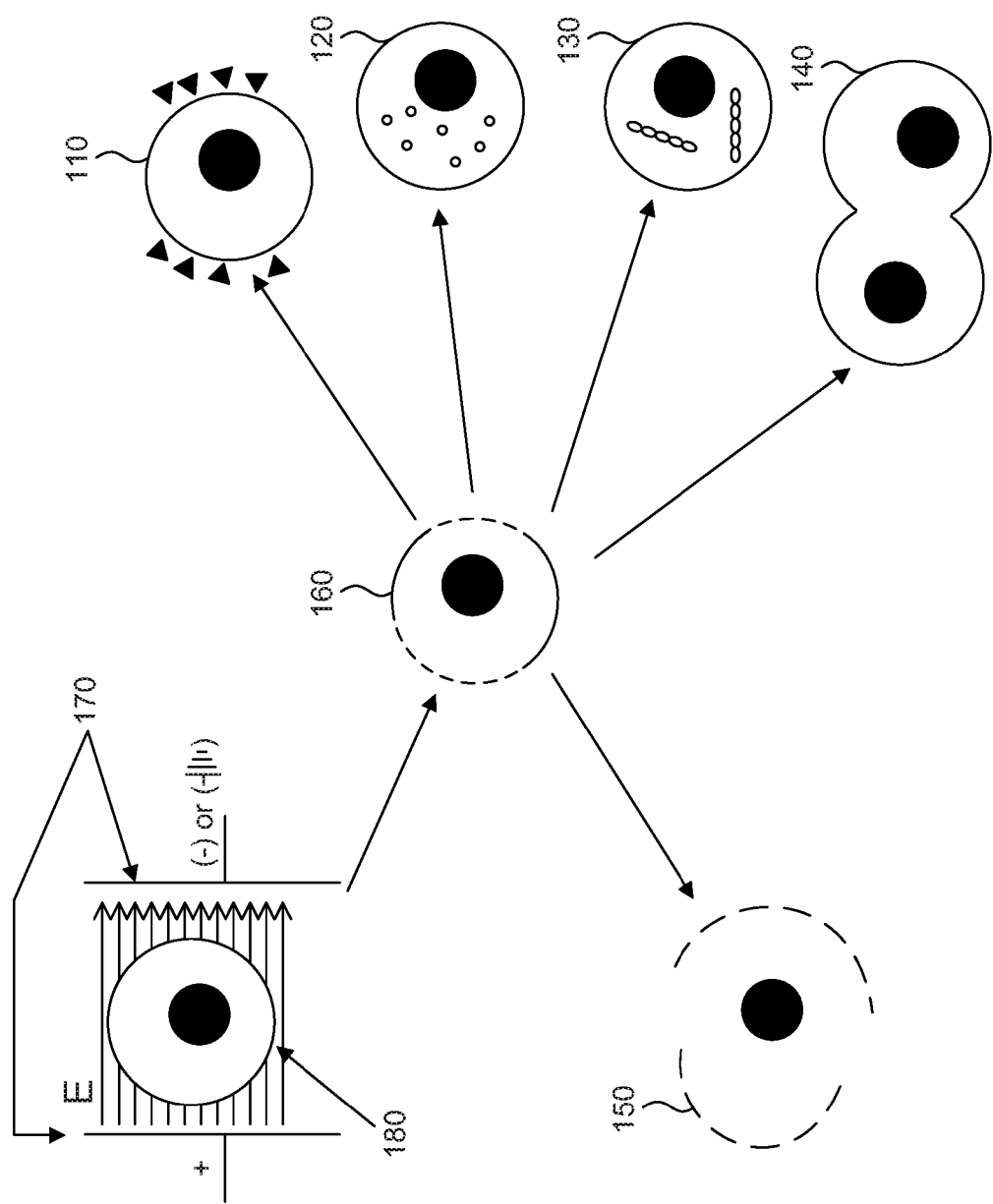
FIG. 1 illustrates a number of applications of electroporation.

FIG. 1 illustrates a number of applications of electroporation (FIG. 1 has been adapted from material presented in a March 2008 lecture by Dr. Damijan Miklavcic. See http://videolectures.net/tict08_miklavcic_ebt/). The main use of electroporation-based technologies and treatments in modern medicine and industrial applications are: molecular cell biology research, cell fusion, gene expression silencing by small interfering RNA (siRNA), electrochemotherapy, protein insertion into a cell membrane, gene therapy based on electro-gene transfer, various applications within biotechnology, tissue ablation, cell fusion for monoclonal antibody production, water and liquid food sterilization, and transdermal drug delivery.

Electrochemotherapy is the combination of chemotherapy and electroporation during which an electric pulse generator is used to apply an electrical current through electrodes that are inserted into the body on either side of a cancerous tumor. A chemotherapy drug is then injected near the tumor site such that the chemotherapeutic surrounds the cell. Once the electric pulse is applied from the generator through the electrodes, the increase in cell membrane permeability allows access to the cytosol (intracellular fluid). If the pulsed current amplitude and duration is carefully moderated, then the pores of the cells can reseal (reversible electroporation) encapsulating the chemotherapeutic. A similar method might be employed with antibiotics and bacterium.

Current methods of electroporation in the application of vital medications, such as during electrochemotherapy, require the electrodes to be inserted into the patient, in addition to the physical introduction of the chemotherapeutic. These procedures can be painful, add extra steps and complexity to the treatment protocol, and are a potential source of infection transmission. Significant collateral cell death and low delivery efficiency have challenged traditional methods of electroporation (Andre, F. M., et al., 2010).

A commonly applied technique for drug delivery through the skin without the use of an injection needle is iontophoresis. Iontophoresis, also known as electromotive drug administration (EMDA), uses a relatively small electric charge to deliver a medication, a chemical agent, or a bioactive agent through a patient's skin. While traditional methods of inducing iontophoresis can be effective in specific circumstances, it is time consuming to administer, can create tingling, irritation or burning in the patient, has a markedly lower efficacy with nonpolar drugs, and requires an intact stratum corneum (outermost layer of the epidermis) for effective drug penetration, which means that it cannot be used on damaged skin. In the context of this disclosure, the word "electroporation" is used to include iontophoresis.

The cold plasma method (including, but not limited to, a multi-frequency harmonic-rich cold plasma treatment) of transdermal electroporation of medication is simple, painless, and an effective method of generating electroporation for the successful introduction of a multitude of medications or bioactive agents to a patient's body or cells. In U.S. Non-Provisional application Ser. No. 13/620,236, filed on Sep. 14, 2012, specific tips are described that are designed to produce plumes of plasma where the delivery of biological materials and agents (viral vectors, DNA, etc.), chemicals or drugs, and proteins in addition to the plasma itself is possible when desirable. The disclosure of U.S. patent application Ser. No. 13/620,236, filed Sep. 14, 2012, is included herein by reference in its entirety.

Figure 5:
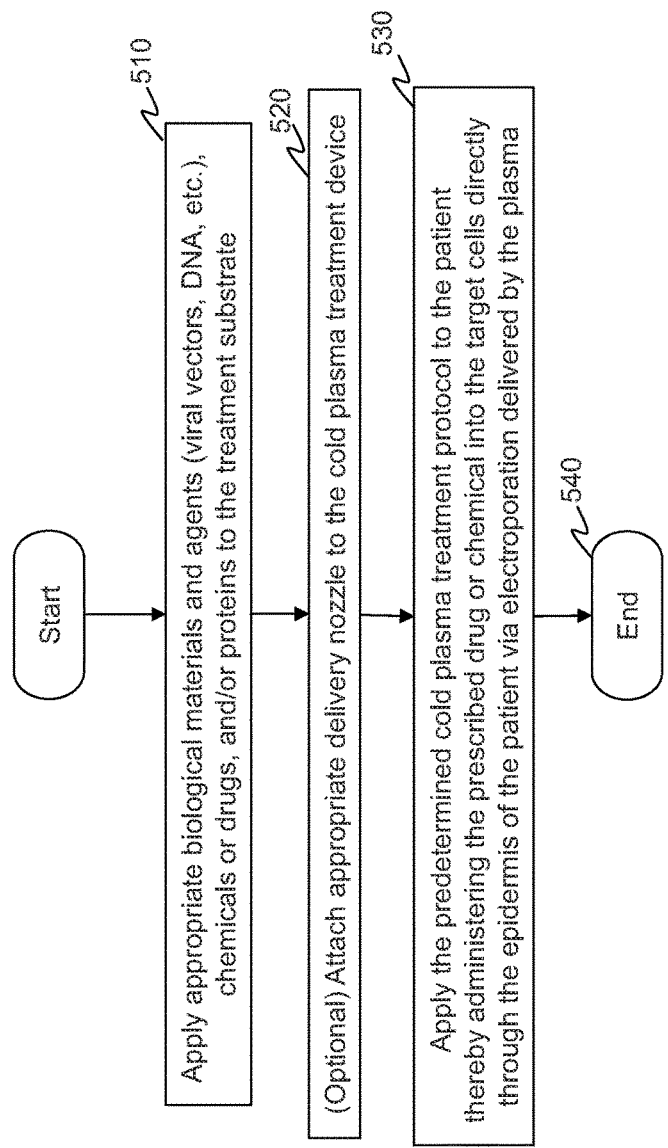
FIG. 5 illustrates a method for electroporation using a cold plasma, in accordance with an embodiment of the present invention.

The prescribed biological materials and agents (viral vectors, DNA, etc.), chemicals or drugs, and/or proteins can be introduced into the patient's body in one of three main cold plasma techniques or methodologies, as described herein. First and simplest, the prescribed material (in liquid, gel, or powdered form) can be applied to the epidermis of the recipient (FIG. 3A and FIG. 5). In this embodiment, the prescribed agent can be lidocaine, ropivacaine, bupivacaine, Marcaine®, or another anesthetic, and the treatment time to achieve therapeutic penetration of the substrate can be 30, 60, or 300 seconds. In an alternative embodiment, the prescribed agent can be an antibiotic with a treatment time of 30, 60, or 300 seconds. In a further alternative embodiment, the prescribed agent can be a chemotherapeutic agent with a treatment of 30, 60, 300, or 600 seconds. The above details are merely exemplary, and not limiting in scope.

A pulsed electrical energy source generates a cold plasma, and the cold plasma, carries a pulsed electrical energy field. When the cold plasma is directed over a recently applied prescribed material, one resulting effect is a controllable state of electroporation in the cells of the target substrate. The consequential increase in cell membrane permeability permits the transfer of the drug or chemical into the target cells.

Figure 2:
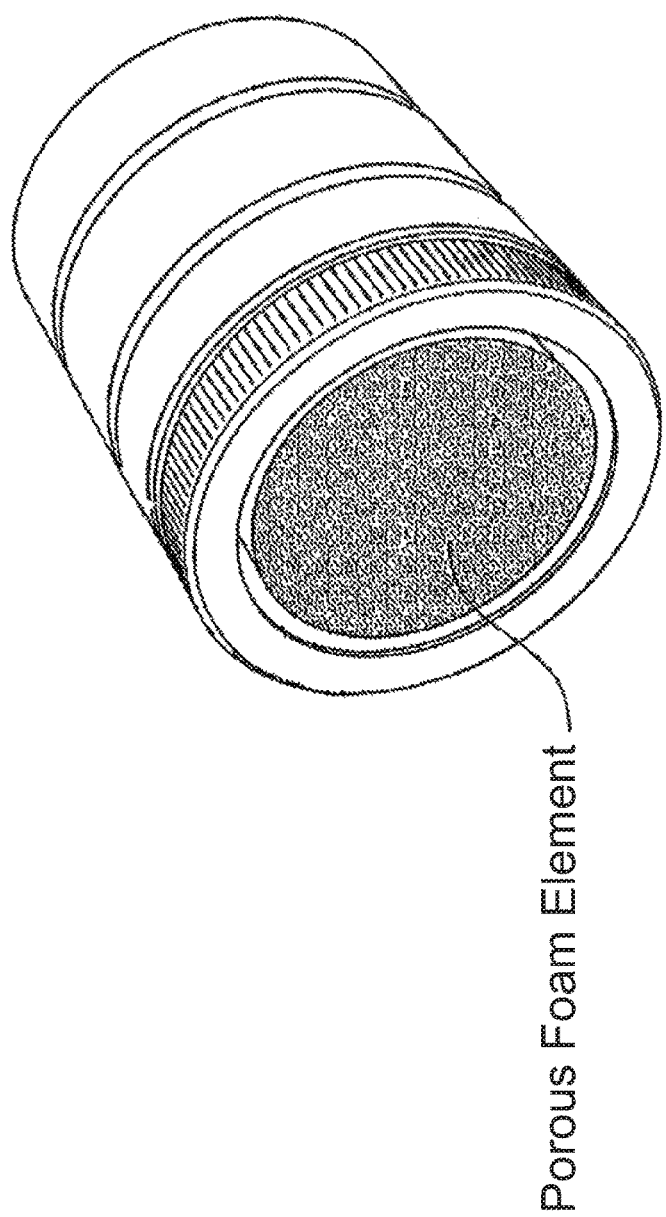
FIG. 2 illustrates an exemplary tip assembly that includes a porous foam element, in accordance with an embodiment of the present invention.

FIG. 2 illustrates a second embodiment of the present invention. Referring to FIG. 2, an expanded graphical view of a 42 mm circumference tip is illustrated for use with a cold plasma generation device. More generally, apertures within the tip may be of any shape, including circular, slit and polygon shapes. Included in the tip is a porous foam, made from a material such as a porous foam or other suitable materials known to one skilled in the art, that is inserted within the assembly. The foam provides a potential carrying mechanism for the inclusion of water, solutions or drugs for introduction into the cold plasma stream, which are then electroporated into the tissues. With the addition of a porous foam element to any of the cold plasma tips (as illustrated in FIG. 2), this treatment method applies the appropriate prescribed biological materials and agents (viral vectors, DNA, etc.), chemicals or drugs, and/or proteins to the porous element, with the result that the patient is treated with the non-thermal plasma for a combined therapy. The prescribed material contained within the porous element would be transported in the cold plasma plume to the target treatment substrate and thereby introduced into the cytosol of the target cells via the electroporation induced by the cold plasma.

FIGS. 3A and 3B illustrate different tips 310, 320 that can be affixed to the outlet port of a cold plasma device. These tips represent examples of different methods of administering a prescribed material to a patient. For example, for the embodiment illustrated in FIG. 3A, prescribed biological materials and agents (viral vectors, DNA, etc.), chemicals or drugs, and/or proteins are first applied to the treatment area on the patient's skin. Next, plasma plume 312 is applied to the treatment area to induce electroporation and thereby deliver the agent or drug to the cells of the patient.

FIG. 3B illustrates an alternative approach, whereby illustrated tip 320 includes a porous foam element, 322, that can be added to any of the cold plasma tips in order to introduce a prescribed agent into the plasma stream for electroporation applications. In both cases, the tips can be either reusable or disposable.

Figure 4:
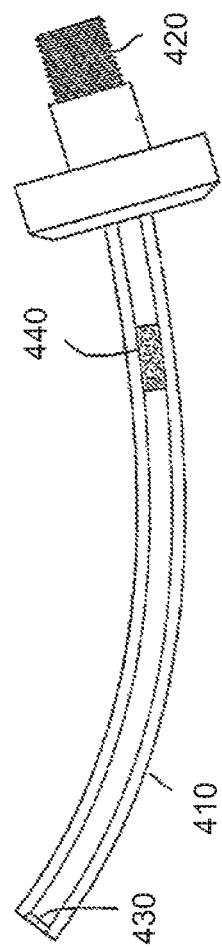
FIG. 4 illustrates a cannula tube embodiment that includes a porous foam element, in accordance with an embodiment of the present invention.

FIG. 4 illustrate a third embodiment of the present invention. Referring to FIG. 4, a cannula tube embodiment is illustrated that can deliver any prescribed agent into a bodily lumen, cavum, vestibule, or buccal cavity via the porous foam elements 440. In this third method of delivery of prescribed biological materials and agents (viral vectors, DNA, etc.), chemicals or drugs, and/or proteins in a non-thermal plasma treatment protocol, the prescribed material can be added to an open-celled foam element that is contained within the main lumen of a cannula device. Not all medical treatments can be performed external to the body of a human or animal. In many cases, the treatment site is internal to a body and access to such a site requires the provision of tools that are placed at the end of various elongated devices, such as laparoscopic, arthroscopic and endoscopic devices.

Continuing to refer to FIG. 4, an exemplary cannula tube 410 can be attached to the outlet port of the cold plasma device. In an exemplary embodiment, cannula tube 410 has a single aperture 420 at the proximal end that is attached to the outlet port of the cold plasma device. Cannula tube 410 has a length sufficient to reach a desired treatment area. Typically, the treatment area is internal to a human being or animal, where the treatment area is accessible via an opening such as mouth, nose, arterial or venal entry point, or transdermally through a port (laproscopic, arthroscopic). Thus, a cannula tube can be used for internal treatment within any bodily lumen, cavum, vestibule or buccal cavity and can be utilized to deliver any appropriate biological materials and agents (viral vectors, DNA, etc.), chemicals or drugs, and/or proteins via the internal open-celled foam element 440. In an embodiment of the present invention, the cannula tube has a single aperture 430 at the distal end inserted into the treatment area. Cannula tube 410 can be used for internal treatment within any bodily lumen, cavum, vestibule, or buccal cavity.

In an alternative embodiment (not shown), the exemplary cannula tube includes a plurality of apertures at the distal end of the cannula tube, and a porous foam element, which can be enriched with the appropriate chemical or drug substance. In various embodiments, the apertures can be at the end or placed at a variety of locations along a portion of the length of the cannula tube adjacent to the end of the cannula tube. In one of these embodiments, the distal end of the cannula tube can be sealed, with one or more apertures located along the body length. Cannula tube can be used for internal treatment along the length of any bodily lumen, cavum, vestibule, or buccal cavity. The placement of open-celled foam element 440 illustrated in FIG. 4 is merely exemplary and not limiting to the scope of various embodiments of the present invention. For example, the placement of a suitable element may be placed in any location consistent with delivery of the biological materials and agents (viral vectors, DNA, etc.), chemicals or drugs, and/or proteins at the desired treatment area. In particular, a suitable element may be placed at a location that is also driven by ease of manufacture, or other considerations. As an example, an element may be placed at the base of the cannula nozzle, where it attaches to the cold plasma applicator device. Further, the shape of the element can take on any form consistent with its placement at any suitable location of the cannula tube.

The type of material noted in open-celled foam element 440 (as illustrated in FIG. 4) is also merely exemplary of the materials that can be used, and not limiting to the scope of various embodiments of the present invention. For example, any material that can act as a reservoir of biological materials and agents (viral vectors, DNA, etc.), chemicals or drugs, and/or proteins while permitting movement of the cold plasma through the material falls within the scope of various embodiments of the present invention.

In addition, various embodiments of the present invention are not limited to a particular cold plasma generation approach. For example, embodiments of the present invention may include cold plasma generation approaches, as well as multi-frequency harmonic-rich cold plasma generation approaches. In addition, different techniques of cold plasma generation are also included. For example, cold plasma generation can include gas-fed plasma generation devices that take as an input a source of an appropriate working gas (e.g., helium or any other suitable gas) and a source of high voltage electrical energy, and output a plasma plume. Previous work by the inventors in this research area has been described in U.S. Provisional Patent Application No. 60/913,369, U.S. Non-provisional application Ser. No. 12/038,159 (that has issued as U.S. Pat. No. 7,633,231) and the subsequent continuation applications ("the '369 application family"). Different high voltage power supplies may also be used to provide the resulting cold plasma (for example, but not limited to, a multi-frequency harmonic-rich supply as described in the '369 application family, and in U.S. patent application Ser. No. 13/620,118, filed Sep. 14, 2012, which is incorporated herein by reference in its entirety). As noted previously, in the context of this application, the methods disclosed herein can be used with any platform for the generation of cold plasma. Accordingly, the methods are not limited to the use of a DBD device, a gas jet device, or a cold plasma generated using a multi-frequency harmonic-rich power supply.

Devices, other than the gas-fed cold plasma generation device described above, can also generate cold plasma. For example, cold plasma can also be generated by a dielectric barrier discharge device, which relies on a different process to generate the cold plasma. A dielectric barrier discharge (DBD) device contains at least one conductive electrode covered by a dielectric layer. The electrical return path is formed by the ground that can be provided by the target substrate undergoing the cold plasma treatment or by providing an in-built ground for the electrode. Energy for the dielectric barrier discharge device can be provided by a high voltage power supply, such as that mentioned above. More generally, energy is input to the dielectric barrier discharge device in the form of pulsed DC electrical voltage to form the plasma discharge. By virtue of the dielectric layer, the discharge is separated from the conductive electrode and electrode etching and gas heating is reduced. The pulsed DC electrical voltage can be varied in amplitude and frequency to achieve varying regimes of operation. Any device incorporating such a principle of cold plasma generation (e.g., a DBD electrode device) falls within the scope of various embodiments of the present invention.

The above embodiments also facilitate an approach that allows for the administration of a cold plasma treatment protocol while the patient is simultaneously undergoing treatment with a systemic drug. When a systemic drug is being prescribed to a patient (such as oral or intravenous (IV) antibiotics or chemotherapy), it may be desirable to also treat a specific area, or multiple areas, with cold plasma. The cold plasma could be applied with or without chemical agents being delivered through electroporation. This combined methodology would allow for the cold plasma to be used at a specific site to treat an infection or tumor with the systemic drug treatment method for a cumulative healing effect.

Figure 6:
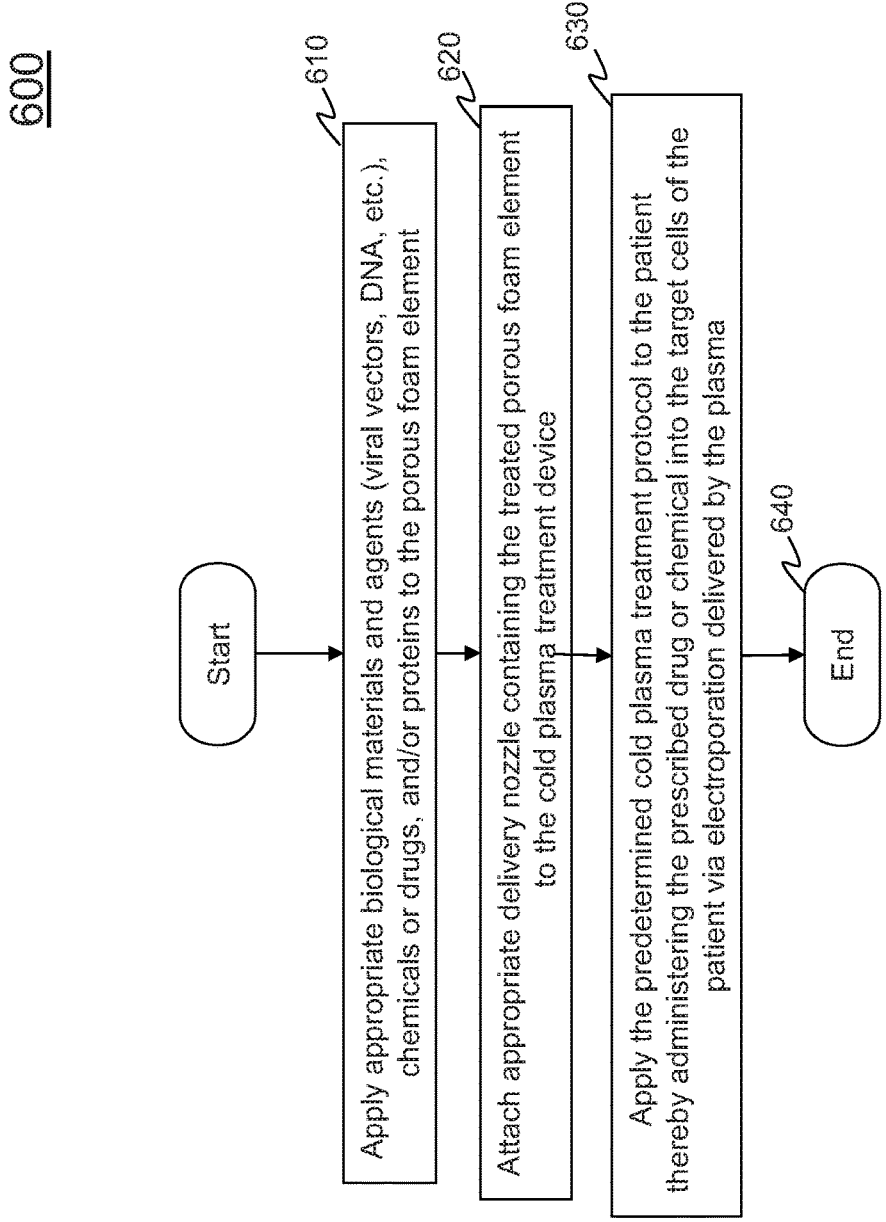
FIG. 6 illustrates a method for electroporation using a cold plasma, in accordance with an embodiment of the present invention.

FIGS. 5 and 6 provide further details of two approaches to the combined methodology. Referring to FIG. 5, a methodology is illustrated for using a cold plasma device for administration of prescribed biological materials and agents (viral vectors, DNA, etc.), chemicals or drugs, and/or proteins treatment in combination with non-thermal plasma when the chemical or drug is applied directly to the patient's skin or treatment substrate. In step 510, appropriate biological materials and agents (viral vectors, DNA, etc.), chemicals or drugs, and/or proteins are applied to the treatment substrate. In step 520, if the cold plasma device is a gas jet device, an appropriate delivery nozzle may be optionally attached to the cold plasma treatment device. In step 530, the predetermined cold plasma treatment protocol is applied to the patient, thereby administering the prescribed drug or chemical directly into the target cells of the patient via electroporation delivered by the cold plasma. Target cells can include the skin, a wound, a surgical site, a structure exposed during a surgical procedure, a tumor, or any tissue that can be contacted directly by the combination of the therapeutic agent and the plasma.

Referring to FIG. 6, a methodology is illustrated for using a cold plasma device for administration of the prescribed biological materials and agents (viral vectors, DNA, etc.), chemicals or drugs, and/or proteins that are applied to a porous foam element. The prescribed materials are introduced to the target cells via electroporation through administration of a non-thermal plasma treatment protocol with a cold plasma device In step 610, appropriate biological materials and agents (viral vectors, DNA, etc.), chemicals or drugs, and/or proteins are applied to the porous foam element. In step 620, an appropriate delivery nozzle containing the treated porous foam element is attached to the cold plasma treatment device. In step 630, the predetermined cold plasma treatment protocol is applied to the patient, thereby administering the prescribed drug or chemical into the target cells of the patient via electroporation delivered by the plasma.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A method, comprising:
generating a cold plasma from a cold plasma device; and
passing the cold plasma from the cold plasma device through a body entry point and via a cannula tube to a treatment area of a patient for a predetermined treatment time, wherein the cannula tube comprises an element positioned in the cannula tube, the element comprising a chemical-or-drug substance and an open-celled foam material configured to absorb the chemical-or-drug substance, and passing the cold plasma through the chemical-or-drug substance thereby causes electroporation of the chemical-or-drug substance into cells of a patient.

2. The method of claim 1, wherein the chemical-or-drug substance comprises at least one of a biological material, agent, viral vector, DNA, chemical, drug, or protein.

3. The method of claim 1, wherein the chemical-or-drug substance comprises at least one of lidocaine, ropivacaine, bupivacaine and an anesthetic.

4. The method of claim 1, wherein the chemical-or-drug substance comprises a chemotherapeutic agent.

5. The method of claim 1, wherein the predetermined treatment time and the chemical-or-drug substance are associated with a treatment protocol.

6. The method of claim 1, wherein the body entry point is a mouth or a nose.

7. The method of claim 1, wherein the body entry point is an arterial entry point or a venal entry point.

8. The method of claim 1, wherein the body entry point is a transdermal entry point obtained using a laproscope or an arthroscope.

9. The method of claim 1, wherein the treatment area is within one of a bodily lumen, a cavum, a vestibule, or a buccal cavity.

10. The method of claim 1, wherein the cannula tube comprises an aperture adjacent to an end of the cannula tube.

11. The method of claim 1, wherein generating the cold plasma from the cold plasma device comprises generating the cold plasma from a multi-frequency harmonic-rich cold plasma generator.

12. The method of claim 1, wherein generating the cold plasma from the cold plasma device comprises generating the cold plasma from a dielectric barrier discharge (DBD) cold plasma generator.

13. The method of claim 1, wherein generating the cold plasma from the cold plasma device comprises generating the cold plasma from a gas jet cold plasma generator.

14. The method of claim 1, wherein the element is located at a base of the cannula tube.

15. The method of claim 1, wherein the cannula tube comprises a plurality of apertures adjacent to an end of the cannula tube.

16. The method of claim 1, wherein the cannula tube comprises a plurality of apertures located along a portion of the cannula tube.

17. The method of claim 1, wherein the treatment area is a surgical site.

18. The method of claim 1, wherein the treatment area includes a tumor.

19. The method of claim 1, wherein the treatment area includes a structure exposed during a surgical procedure.

20. The method of claim 1, wherein the treatment area includes a wound.

* * * * *